United States Patent [19]
Sahota

[11] Patent Number: 6,015,402
[45] Date of Patent: Jan. 18, 2000

[54] WIRE PERFUSION CATHETER

[76] Inventor: Harvinder Sahota, 3861 Wisteria St., Seal Beach, Calif. 90740

[21] Appl. No.: 09/090,504

[22] Filed: Jun. 4, 1998

Related U.S. Application Data

[62] Division of application No. 08/813,478, Mar. 7, 1997, Pat. No. 5,800,393.

[51] Int. Cl.$^7$ .................................................. A61M 25/00
[52] U.S. Cl. ................................. 604/523; 604/96; 623/1
[58] Field of Search .................................... 604/523, 524, 604/525, 526, 527, 532, 536, 96, 500; 623/1, 12, 66

[56] References Cited

U.S. PATENT DOCUMENTS

| | | |
|---|---|---|
| 2,930,377 | 3/1960 | Cowley . |
| 3,045,677 | 7/1962 | Wallace . |
| 3,173,418 | 3/1965 | Baran . |
| 3,448,739 | 6/1969 | Stark et al. . |
| 3,834,394 | 9/1974 | Hunter et al. . |
| 3,868,956 | 3/1975 | Alfidi et al. ............................ 604/532 |
| 3,889,686 | 6/1975 | Duturbure . |
| 4,029,104 | 6/1977 | Kerber . |
| 4,040,413 | 8/1977 | Ohshiro . |
| 4,224,929 | 9/1980 | Furihata . |
| 4,233,983 | 11/1980 | Rocco . |

(List continued on next page.)

FOREIGN PATENT DOCUMENTS

| | | |
|---|---|---|
| 0214721 | 3/1987 | European Pat. Off. . |
| 344530 | 12/1989 | European Pat. Off. . |
| 8303766 | 4/1983 | WIPO . |
| 8800071 | 1/1988 | WIPO . |
| 8803817 | 6/1988 | WIPO . |

OTHER PUBLICATIONS

Dorros, Gerald MD, et al., "Probe™, a Balloon Wire: Initial Experience", Catheterization and Cardiovascular Diagnosis, 14:286–288 (1988).

King, Spencer B. MD; Douglas, John S. Jr. MD, *Coronary Arteriography and Angioplasty*, McGraw–Hill Book Company, pp. 399–460.

Simpson, John B., et al., "A New Catheter System for Coronary Angioplasty", *The American Journal of Cardiology*, vol. 49, pp. 1216–1222, Apr. 1, 1982.

"Balloon Dilatation for Congenital Pulmonary Valve Stenosis", Cardiology Product News, p. 3, Jan. 1983.

Abstract of WO89/03701, Harmjanz D.

*C.R. Bard, Inc. v. Advanced Cardiovascular Systems, Inc.*, Case No. 89–1719 decided Aug. 2, 1990.

"Cordis Infusion Catheter Set: A simple, reliable system for thrombolysis of coronary and other arteries", ©Cordis Corporation, 1982.

"Bourassa Cardiovascular Catheters Sterile", USCI, 1972.

"USCI™ Gruntzig Dilaca™ Coronary Balloon Dilatation Catheters, New Coronary Balloons for New Coronary Challenges", ©C.R. Bard, Inc. 1982.

(List continued on next page.)

*Primary Examiner*—John D. Yasko
*Attorney, Agent, or Firm*—Knobbe, Martens, Olson & Bear LLP

[57] ABSTRACT

A low profile wire perfusion catheter is disclosed for use in percutaneous transluminal coronary angioplasty. The catheter includes a wire configured to be inserted into a blood vessel. The wire is hollow and defines an axial lumen therein. An inflation balloon is attached directly to the wire and is configured to expand radially outward in response to inflation thereof. Inflow and outflow perfusion ports extend through the wire and communicate with the lumen to allow perfusion of blood across the balloon when the balloon is inflated within a blood vessel. Because the balloon is attached directly to the wire, the catheter has an advantageously low cross-sectional area.

5 Claims, 5 Drawing Sheets

U.S. PATENT DOCUMENTS

| | | |
|---|---|---|
| 4,323,071 | 4/1982 | Simpson et al. . |
| 4,328,056 | 5/1982 | Snooks . |
| 4,329,993 | 5/1982 | Lieber et al. . |
| 4,338,930 | 7/1982 | Williams . |
| 4,403,612 | 9/1983 | Fogarty . |
| 4,423,725 | 1/1984 | Baran et al. . |
| 4,445,892 | 5/1984 | Hussein et al. . |
| 4,447,227 | 5/1984 | Kotsanis . |
| 4,461,280 | 7/1984 | Baumgartner . |
| 4,467,790 | 8/1984 | Schiff . |
| 4,527,549 | 7/1985 | Gabbay . |
| 4,546,759 | 10/1985 | Solar . |
| 4,547,193 | 10/1985 | Rydell . |
| 4,563,181 | 1/1986 | Wijayarathna et al. . |
| 4,564,014 | 1/1986 | Fogarty et al. . |
| 4,573,966 | 3/1986 | Weikl et al. . |
| 4,581,017 | 4/1986 | Sahota . |
| 4,608,984 | 9/1986 | Fogarty . |
| 4,610,662 | 9/1986 | Weikl et al. . |
| 4,644,936 | 2/1987 | Schiff . |
| 4,655,771 | 4/1987 | Wallsten ................................ 623/1 |
| 4,689,040 | 8/1987 | Thompson . |
| 4,737,153 | 4/1988 | Shimamura et al. . |
| 4,738,666 | 4/1988 | Fuqua . |
| 4,744,366 | 5/1988 | Jang . |
| 4,762,129 | 8/1988 | Bonzel . |
| 4,763,654 | 8/1988 | Jang . |
| 4,771,777 | 9/1988 | Horzewski et al. . |
| 4,784,639 | 11/1988 | Patel . |
| 4,785,815 | 11/1988 | Cohen . |
| 4,808,155 | 2/1989 | Mahurkar . |
| 4,822,345 | 4/1989 | Danforth . |
| 4,824,435 | 4/1989 | Giesy et al. . |
| 4,826,480 | 5/1989 | Diaz et al. . |
| 4,842,589 | 6/1989 | Fecht et al. . |
| 4,877,031 | 10/1989 | Conway et al. . |
| 4,892,519 | 1/1990 | Songer et al. . |
| 4,909,252 | 3/1990 | Goldberger . |
| 4,932,413 | 6/1990 | Shockey et al. . |
| 4,950,239 | 8/1990 | Gahara et al. . |
| 4,960,411 | 10/1990 | Buchbinder . |
| 4,976,690 | 12/1990 | Solar et al. . |
| 4,983,167 | 1/1991 | Sahota . |
| 4,988,356 | 1/1991 | Crittenden et al. . |
| 5,000,734 | 3/1991 | Boussignac et al. . |
| 5,000,743 | 3/1991 | Patel . |
| 5,002,531 | 3/1991 | Bonzel . |
| 5,019,042 | 5/1991 | Sahota . |
| 5,046,503 | 9/1991 | Schneiderman . |
| 5,071,406 | 12/1991 | Jang . |
| 5,087,247 | 2/1992 | Horn et al. . |
| 5,090,958 | 2/1992 | Sahota . |
| 5,090,960 | 2/1992 | Don Michael . |
| 5,092,873 | 3/1992 | Simpson et al. . |
| 5,137,513 | 8/1992 | McInnes et al. . |
| 5,147,377 | 9/1992 | Sahota . |
| 5,158,548 | 10/1992 | Lau et al. ................................ 604/523 |
| 5,160,321 | 11/1992 | Sahota . |
| 5,163,906 | 11/1992 | Ahmadi . |
| 5,169,395 | 12/1992 | Narciso, Jr. . |
| 5,226,889 | 7/1993 | Sheiban . |
| 5,314,418 | 5/1994 | Takano et al. ........................ 604/524 |
| 5,320,605 | 6/1994 | Sahota . |
| 5,370,617 | 12/1994 | Sahota . |
| 5,395,333 | 3/1995 | Brill . |
| 5,417,653 | 5/1995 | Sahota et al. . |
| 5,716,340 | 2/1998 | Schweich, Jr. et al. . |

OTHER PUBLICATIONS

"USCI™ Probing Catheter", ©C.R. Bard, Mar. 1988.
"USCI Positrol II™ & Nycore™ Cardiovascular Catheters", ©C.R. Bard, Inc. 1980.
"USCI Gruntzig Dilaca™ Coronary Dilatation Equipment", ©C.R. Bard, Inc., 1981.
"USCI Gruntzig Dilaca™ Coronary Dilatation Equipment", ©C.R. Bard, Inc., 1982.
"USCI Gruntzig™ Steerable Balloon Dilatation System", ©C.R. Bard, Inc. 1982.
"USCI Gruntzig™ Femoral, Iliac and Gruntzig Dilaca™ Renal Dilatation Catheters", ©C.R. Bard, Inc. 1980.
"USCI Safety Spring Guides", ©C.R. Bard, Inc. 1979.
"The Simpson–Robert™ Vascular Dilation System For Percutaneous Transluminal Coronary Angioplasty (PTCA)", Advanced Catheter Systems, Inc., Aug. 1981.

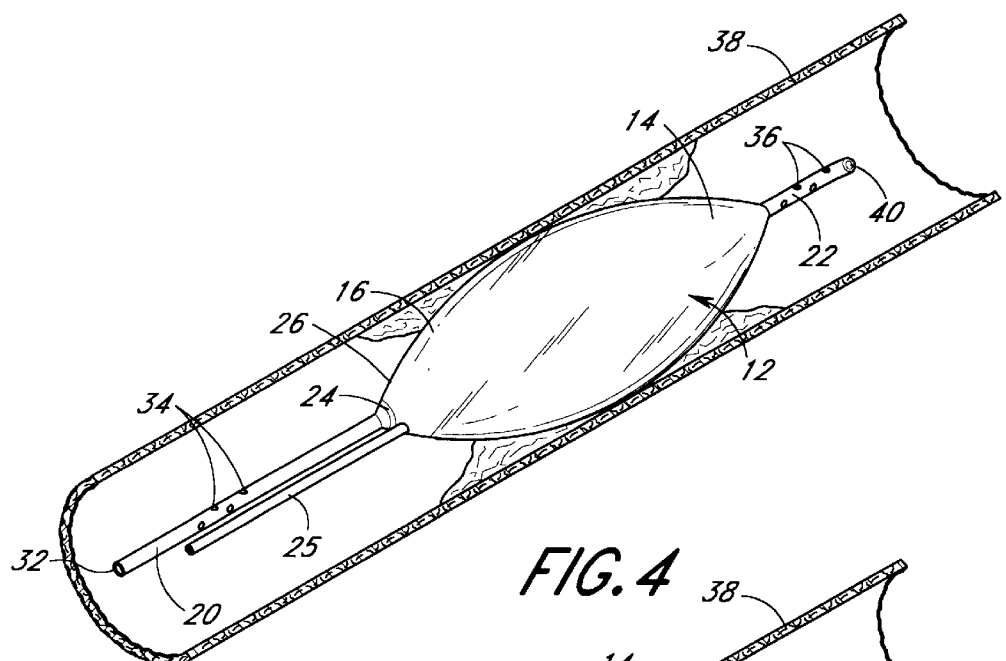
FIG. 4
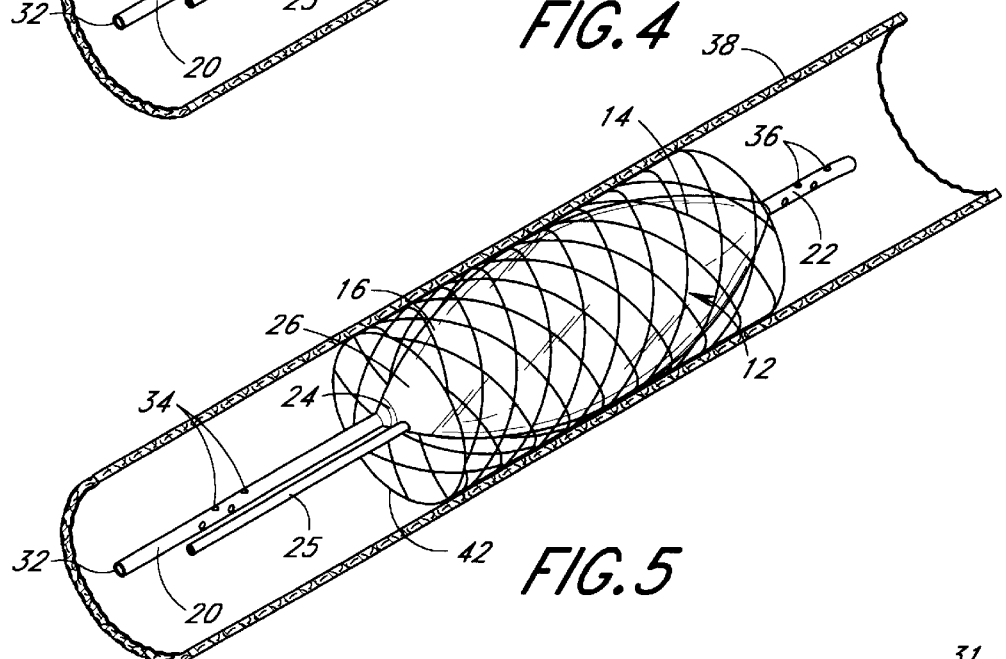
FIG. 5
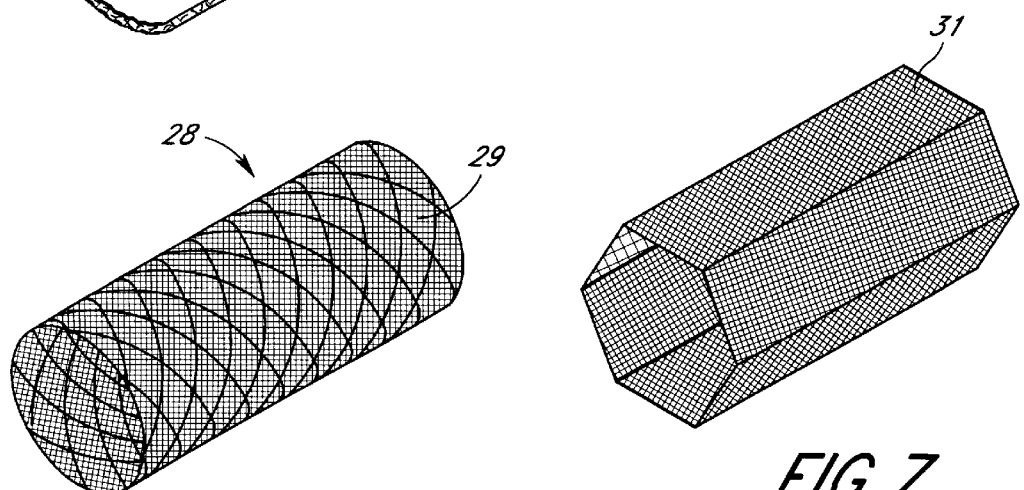
FIG. 6
FIG. 7

WIRE PERFUSION CATHETER

This application is a divisional of Ser. No. 08/813,478 filed Mar. 7, 1997 now U.S. Pat. No. 5,800,393.

BACKGROUND OF THE INVENTION

1. Field of the Invention

The present invention relates to the field of balloon catheters, and in particular relates to a low-profile dilation perfusion catheter.

2. Description of the Related Art

Percutaneous transluminal coronary angioplasty (PCTA) is a procedure for treating a stenosis or a narrowed region in a coronary artery. PCTA is often used as an alternative to coronary bypass surgery. A main advantage of PCTA is the avoidance of many of the post-operative problems associated with such surgery. Moreover, there is a reduction of morbidity with the use PCTA over bypass surgery.

In one form, PCTA involves the use of a catheter having an expandable balloon attached to its distal end. The catheter is inserted into an artery, such as into the femoral artery, and advanced transluminally through the artery until the balloon is positioned adjacent the narrowed portion of the artery. The balloon is thereafter inflated using an inflation medium that is advanced through a lumen within the catheter. The balloon expands radially outward to displace the obstruction in the artery. If the stenosis is composed primarily of fatty deposits, it is possible to compress the stenosis against the arterial wall and thereby restore a portion or all of the original interior diameter of the artery.

Unfortunately, there are certain drawbacks associated with such a procedure. When the balloon is inflated, it completely occludes the blood flow within the artery. However, it is undesirable to occlude an artery for extended periods of time. The cessation of blood flow caused by the dilated balloon presents a high risk of damage to the portions of the body downstream of the occlusion, particularly the heart. Hence, the balloon may only be pressurized for a few seconds at a time in order to avert any damage downstream of the occlusion due to the absence of blood flow. A balloon catheter treatment thus involves cyclically inflating and deflating the balloon for short periods of time until the desired results are achieved.

SUMMARY OF THE INVENTION

For certain treatments it is desirable to inflate the balloon for longer periods of time. For instance, a greater inflation period provides a stent with a more uniform shape after the balloon is removed, which preferably reduces the likelihood of the stent collapsing at a later time, which may result in undesired complications. Furthermore, an increased dilation period is also desirable in order to avoid trauma that may occur to arterial walls as a result of the repeated inflation and deflation of the balloon.

Perfusion catheters are other to allow blood flow across an inflated balloon. Such a catheter has a balloon that is attached to an elongated, hollow catheter body. The hollow body defines a passage that is configured to receive a guidewire. The guidewire is percutaneously routed to the site of the stenosis. The catheter is then routed over the guide wire so that the catheter body "rides" over the guide wire to the stenosis site. To solve the problem of the occlusion of blood flow across the inflated balloon, perfusion ports are employed at locations proximal and distal of the balloon. The ports communicate with the inflation lumen and thereby place the proximal end of the balloon in fluid communication with the distal end of the balloon. In this manner, blood is allowed to perfuse across the balloon through the lumen so that blood flows beyond the balloon even when the balloon is inflated. This provides for longer balloon inflation periods as blood continues to flow across the inflated balloon.

Unfortunately, such catheters have a high cross-sectional area or profile. The extra space for perfusion increases the cross-sectional area of the catheter. When the catheter is used to deploy an ostial stent (or other type of stent), the profile of the catheter is increased even more by the stent, which is-positioned over the balloon and adds mass to the balloon body. Catheters having high profiles are difficult to introduce into the most distal arteries, which have narrow diameters.

In addition, there is a need for a perfusion catheter having a low profile in order to allow the catheter to be used in distal arteries and other body lumen having very narrow diameters.

The present invention provides a perfusion balloon catheter having a particularly low profile. In one aspect of the invention, a balloon catheter has an axially elongate wire that is suitable for insertion into a blood vessel. The wire is hollow so that it defines an axially extending lumen extending through the wire. An inflation balloon is directly attached to the wire to advantageously provide a low profile to the balloon catheter. This configuration is known as a fixed wire balloon. The balloon is configured to expand radially outward. At least one influent port extends through the wire on a first side of the balloon so that the effluent port is in fluid communication with the lumen in the wire. At least one effluent port extends through the wire on a second side of the balloon so that the effluent port is also in fluid communication with the lumen. Blood may advantageously perfuse across the balloon through the lumen by way of the influent and effluent ports. The balloon catheter may be a multi-lobed balloon. Also, an ostial stent may be mounted over the balloon.

In one embodiment, at least a portion of the axially elongate wire may be formed of a porous material. Preferably, the pores are configured to allow the passage of blood through the pores across the balloon. The pores may replace the influent and effluent perfusion ports to allow blood perfusion across the balloon.

In another aspect of the invention, a catheter includes a first axially elongate wire suitable for insertion into a blood vessel. A lumen extends axially through the wire. An inflation lumen is adjacent, and preferably attached, to the wire. An interior region of the balloon is in fluid communication with the inflation lumen. At least one influent port extends through the wall of the wire proximal of the balloon and at least one effluent port extends through the wall of the distal of the balloon. The influent and effluent ports allow perfusion of blood into and out of the wire. The central lumen in the wire allows blood to flow across the balloon. In one embodiment, a movable wire is located adjacent the first axially elongate wire. The movable wire is contiguous with and slidingly secured to the first axially elongate wire.

In yet another aspect of the invention, a balloon catheter includes an axially elongate wire suitable for insertion into a blood vessel. The wire is hollow and defines a lumen extending axially therethrough. An inflation balloon is directly attached to the wire. The balloon has a proximal end and a distal end, where the proximal end of the inflation balloon integrally forms an elongate catheter shaft that is contiguous with the wire. Means is provided for perfusing blood through the lumen from the proximal end of the balloon to the distal end of the balloon.

These and other features of the invention will now be described with reference to the drawings of preferred embodiments of the wire perfusion catheter. The illustrated embodiments of the wire perfusion catheter are intended to illustrate, but not to limit the invention.

BRIEF DESCRIPTION OF THE DRAWINGS

FIG. 4 illustrates a balloon catheter of an alternate embodiment of the present invention.

FIG. 5 illustrates a balloon catheter of the present invention depicted in an artery with an ostial stent deployed on the balloon;

FIG. 6 illustrates an improved stent having a mesh covering;

FIG. 7 illustrates an improved stent having a hexagonal cross-section;

DETAILED DESCRIPTION OF THE PREFERRED EMBODIMENT

Figure 1:
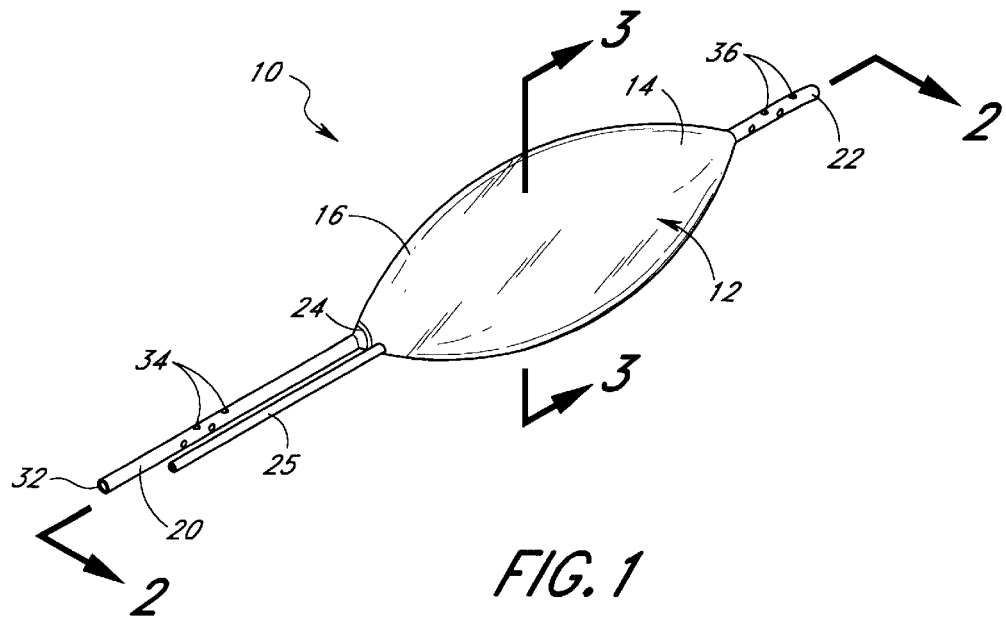
FIG. 1 illustrates a balloon catheter in accordance with a first embodiment of the present invention.

FIG. 1 illustrates a dilation catheter 10 in accordance with a first embodiment of the present invention. The dilation catheter 10 includes a balloon 12 which has a distal end 14 and a proximal end 16. The balloon 12 is mounted directly on an axially elongate wire 20. This configuration is often referred to as a fixed wire balloon catheter because the balloon 12 is mounted directly on the wire 20. Fixed wire balloon catheters have advantage of potentially having a very small cross-sectional area which may be inserted into very narrow arteries or other lumen in the body. The low profile may even allow use in vessels and small body lumen such as bile ducts. However, fixed wire balloons are often less preferable due to the availability of over-the-wire perfusion catheters which allow blood to bypass the balloon, even while the balloon is inflated. Such perfusion catheters are known and described in U.S. Pat. Nos. 4,581,017, 5,090,958, 5,160,321, and 5,370,617. Perfusion catheters, on the other hand, have been limited to larger lumen due to the larger catheter cross-section. The present invention relates to a method and apparatus to provide perfusion in a fixed wire catheter. The construction of fixed wire balloons is known. The balloon 12 is attached to a wire 20 by a suitable means known in the art. The wire 20 extends through the length of the balloon 12 and also extends beyond the distal end 14 to define an advance wire 22. The advance wire 22 may have a variety of lengths and is configured to assist and guide the insertion of the catheter 10 into a body lumen.

The balloon proximal end 16 and distal end 14 taper to approximately the size of the wire 20 and integrally form onto the wire 20. An inflation lumen 25 for selective inflation and deflation of the balloon 12 is positioned adjacent the wire 20 proximally of the balloon. Alternatively, the proximal end 16 may be attached directly to a catheter shaft which surrounds wire 20 and inflation lumen 25, as well understood in the art.

Figure 2:
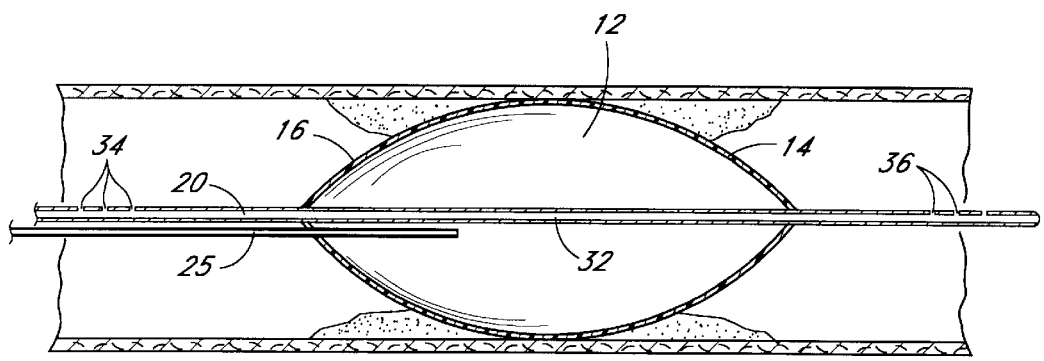
FIG. 2 illustrates the a cross-section of catheter of FIG. 1 in a body lumen such as an artery.

FIG. 2 depicts the cross-section through 2—2 in FIG. 1 and depicts the catheter in a body lumen in cross-section. As depicted in FIG. 2, the wire 20 extends through the balloon with the balloon mounted on the wire. The inflation lumen 25 enters the balloon 12 at the proximal end and opens into the interior of the balloon 12 to provides inflation media for the balloon 12. Such configuration is understood in the art.

Figure 3:
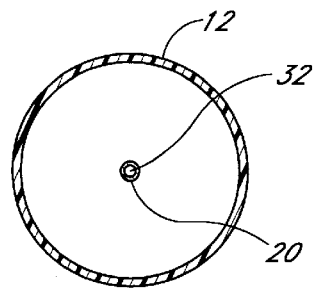
FIG. 3 illustrates a cross-section along 3—3 of FIG. 1.

FIG. 3 is a cross-section of the balloon through 3—3 of FIG. 1.

Preferably, the balloon 12 is formed of a relatively noncompliant material. For instance, the balloon may be formed of thin polyvinyl chloride, polyethylene teraphthalate, nylon, or duralyn. The balloon 12 may be manufactured of any wide variety of other medical grade materials known to those skilled in the art. The balloon 12 is designed to inflate to a known diameter at a given pressure and has a relatively high burst point. The length of the balloon may vary depending upon the particular ostial lesion to be treated and the individual patient characteristics. The balloon 12 may take on a variety of different shapes and sizes that are configured to the stenosis and the particular anatomy of a variety of blood vessels, such as the carotid artery, and other body lumen.

A radiopaque marker 24 may be located on the balloon 12 or guide wire 20 in order to facilitate positioning of the catheter 10 within an artery, as is known in the art. The marker 24 may be manufactured of a variety of materials known to those skilled in the art, such as platinum, gold, or tungsten alloy.

The wire 20 may be manufactured of any wide variety of medical grade materials. As discussed below, the type of material for and characteristics of the wire 20 may be varied along different portions of the wire, such as the portion of the wire that extends through the balloon 12. The length of the wire 20 may vary depending upon the desired application. For PCTA applications, typical lengths range in the area of about 120 cm to 140 cm. The wire 20 may have any wide variety of diameters configured to fit within the walls of an artery. It will be appreciated that smaller wire diameters can decrease the overall profile of the catheter 10.

In accordance with one embodiment of the invention, the wire 20 is hollow so that it defines a passage 32 (best shown in FIG. 2) that extends through at least a portion of the wire proximal of the balloon, through the balloon and distal to the balloon. One or more inflow perfusion ports 34 extend through the wire wall near the proximal end 16 of the balloon 12. The inflow ports 34 are in fluid communication with the passage 32 within the wire 20. One or more effluent perfusion ports 36 extend through the advance wire 22 wall distal of the distal end 14 of the balloon 12 and communicate with the passage 32. The inflow ports 34 and effluent ports 36 allow for fluid flow across the balloon 12 through the passage 32. The number and size of inflow ports 34 and effluent ports 36 may be varied according to the application, and remain within the scope of the invention.

As shown in FIG. 2, the balloon 12 is positioned within a restricted area of an artery 38, such as a stenosis, and inflated using an inflation media that is transferred through the inflation lumen 25. Preferably, the balloon 12 is inflated to a diameter such that the balloon 12 presses against the lumen walls to compress the stenosis. As shown, in an inflated state, the balloon 12 would completely occlude the flow of blood through the artery 38. The influent ports 34 advantageously allow blood to flow into the wire 20, across the balloon 12 and out through the effluent ports 36, even when the balloon 12 is inflated. Specifically, blood flows through the influent ports 34 as the blood approaches the proximal end 16 of the inflated balloon 12. The blood then flows into the passage 32 within the wire 20 and across the balloon 12 where the blood exits the passage 32 through the effluent perfusion ports 36. The blood then flows through the artery vessel. Because the balloon 12 is mounted directly on the wire 20, the catheter 10 can have a very low profile so that the catheter 10 may be used in distal arteries having extremely low diameters or for other body lumen. Yet, due to perfusion, the catheter 10 advantageously allows for increased dilation periods.

FIG. 4 illustrates an alternative embodiment of the present invention. In this embodiment, the effluent ports 34 are replaced or augmented by an axial aperture 40 located at the distal tip of the advance wire 22. In this embodiment, when the balloon 12 is inflated, blood flows through the influent ports 34 and across the balloon 12 through the passage 32. The blood then exits the passage 32 through the effluent aperture 40 at the distal tip of the advance wire 22, and if present, through the effluent ports 36. Accordingly, the advance wire 22 may contain a combination of both effluent ports 36 on the side of the advance wire 22 and an effluent axial aperture 40 at the tip of the advance wire 22.

As an alternative to providing the wire 20 with influent ports 34 and effluent ports 36, the walls of the wire 20 may be manufactured of a porous material that allows fluid communication between the distal and proximal ends 14 and 16 of the balloon 12. In this embodiment, pores extend through the portions of the wall of the wire 20 that are located immediately proximal and distal of the balloon 12. Preferably, the pores are sufficiently large to allow blood to flow into and out of the passage 32. The portion of the wire 20 that is located within the balloon 12 may be formed of a non-porous material so that the wire retains the blood as it flows across the balloon 12 and allows pressure in the balloon. Hence, blood flows into the pores at a location proximal of the balloon 12, through the passage 32 across the balloon, and out of the pores at a location distal of the balloon 12.

FIG. 5 depicts the catheter of the present invention in combination with an ostial stent 42 to scaffold a flow limiting dissection in a blood vessel. Other types of stents could also be used. Advantageously, the stent 42 is mounted directly on the balloon 12. The stent 42 increases the cross-sectional area of the catheter 10 by adding additional material to the surface of the balloon. The reduced profile of the present invention that is achieved by mounting the balloon 12 directly to the wire advantageously allows the use of a stent with a perfusion catheter while providing a reduced cross-sectional area so that the stent 42 may be deployed in narrow lumen.

The stent 42 is deployed in a lumen by first mounting the stent 42 on the balloon catheter 10. The balloon catheter 10 is then percutaneously advanced to the treatment site. An inflation media is used through the inflation lumen 25 to dilate the balloon, which causes the stent 42 to enlarge to the desired size. The stent 42 remains in the artery after removal of the catheter 10 as known in the art. Because of the perfusion capability via the fixed wire 20, a prolonged stent dilation period is possible. A prolonged stent dilation period provides more uniformity to the expanded shape of the stent 42 subsequent to removal of the balloon 12. This advantageously reduces the likelihood of atheroma, and preferably results in-the reduction of thrombus and other complications. Moreover, once the stent 42 is delivered, the operator may remove the balloon 12 with less concern for immediate closure due to thrombus, as the prolonged dilation period of the stent 42 preferably reduces the likelihood of the stent 42 losing its expanded shape.

The stent 42 may be deployed within a vessel on either a permanent or temporary basis. The size of the stent 42 may be varied according to the particular treatment site and balloon with which the stent 42 is to be used. Any wide variety of material known to those skilled in the art may be used to manufacture the stent 42. If the stent 42 is to be deployed within the artery on a temporary basis, it is envisioned that the stent 42 may be manufactured of a material that is configured to eventually dissolve after a desired period of time within the artery.

Heparin could also be used with the present invention to reduce the likelihood of occlusion or obstruction thrombus. The balloon 12 could be coated with heparin, as well as portions or all of the wire 20. When the catheter 10 is used to deploy a stent 40, the stent 40 may also be coated with heparin.

FIG. 6 depicts an alternative embodiment of a stent 28. The stent 28 advantageously has a mesh 29 which covers the stent 28 or is integral with the stent. The mesh 29 advantageously minimizes endothelium from protruding through the stent grid. Furthermore, the mesh advantageously reduces the rate of restenosis.

FIG. 7 depicts yet another embodiment of a stent 31. The stent 31 has an hexagonal cross-section. The hexagonal shape advantageously provides added strength over a circular axial cross-section. This hexagonal shape, thereby, decreases the risk of the stent collapsing partially or fully within the artery or other body lumen.

Preferably, the stents 28, 31 of FIGS. 6 and 7 can be made of any variety of the known stent materials. The hexagonal stent 31 can be made with or without the mesh described with reference to FIG. 6.

Figure 8:
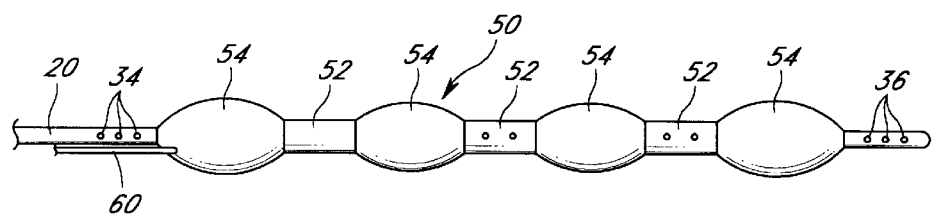
FIG. 8 illustrates a multi-lobed balloon catheter made in accordance with the present invention.

FIG. 8 illustrates yet another embodiment of the present invention in which a multi-lobed dilation balloon 50 is mounted directly on an elongate hollow wire 22. In one embodiment, the multi-lobed balloon is a continuous balloon having alternating regions of thick 52 and thin 54 balloon material. When the balloon 50 is inflated, the thick portions 52 do not expand as readily as the thin portions 54. Hence, the dilation catheter 50 exhibits multiple lobes 54 when inflated. Such a balloon is particularly useful for dilating tortuous vessels that have acute bends. When inflated, the thin portions 54 advantageously dilate stenotic regions by expanding radially outward to a desired diameter, while the thick portions 52, which are resistant to expansion, do not straighten arterial bends. The thick and thin regions 52 and 54 may have a variety of different lengths depending upon the desired characteristics of the multi-lobed balloon. The thick portion may comprise restrictions on a balloon or be part of the balloon itself. Alternatively, the lobes may be formed with individual balloons mounted to the fixed wire 20. The multi-lobed balloon 50 may be used alone in a PCTA treatment or, alternatively, the balloon may be used in combination with an ostial stent. The profile of the multi-lobed balloon catheter has the capability of being very small because the multi-lobed balloon is mounted directly to the wire. Furthermore, the influent ports 34 and effluent ports 36 provide fluid communication between the distal, as in the previous embodiment, and proximal ends of the multilobed balloon 50 to allow blood perfusion across the balloons when inflated. An inflation lumen 60 is provided to inflate the lobes.

Other variations of the multi-lobed balloon or further details are provided in U.S. Pat. No. 5,019,042, issued May 28, 1991, which is herein incorporated by reference.

Figure 9:
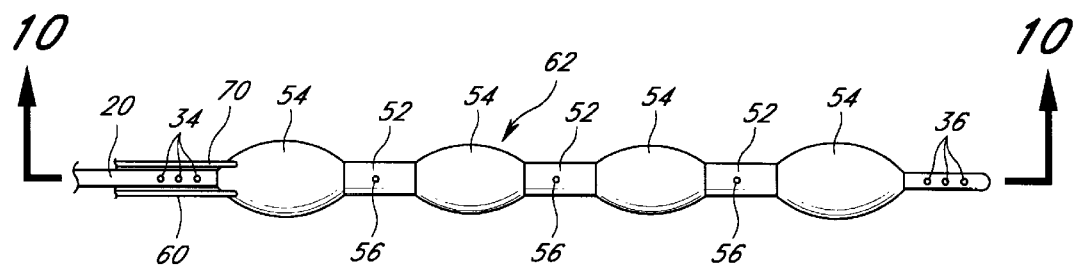
FIG. 9 illustrates another embodiment of a balloon catheter at FIG. 8 made in accordance with of the present invention.
Figure 10:
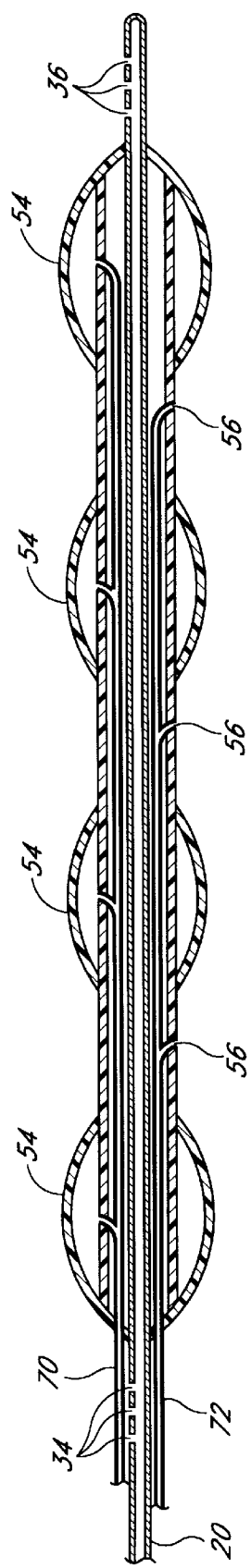
FIG. 10 is a cross-sectional view along 10—10 of FIG. 9.

FIG. 9 illustrates an additional embodiment for the multi-lobed balloon catheter 62 for site-specific parenteral delivery of medication or testing substances to a blood vessel. FIG. 10 is a cross-section of the multi-lobed balloon of FIG. 9. An inflation lumen 70 is in fluid communication with the balloons 54. A delivery lumen 72 is in fluid communication with delivery apertures 56 positioned between one or more balloons 54. In addition, in the embodiment depicted in FIGS. 9 and 10, influent perfusion ports 34 are provided proximally of the balloons 54 and effluent profusion ports 36 are provided distally of the balloons 54. The drug delivery ports 56 may be arranged in a variety of different manners. For example, the drug delivery ports 56 could be disposed symmetrically or randomly between the balloons or could be arranged in a single line. The particular arrangement of drug delivery ports depends on the desired drug delivery pattern.

The procedure of delivering drugs involves first positioning the balloon 62 at a desired drug-delivery site within the blood vessel. The balloon 62 is then inflated. Drugs are then introduced at a proximal end of the catheter into the delivery lumen 72. The drugs travel through the delivery lumen 72. The substance is expelled through the drug delivery ports 56 and into the blood vessel. Because the balloons 54 are mounted directly to the wire 20, the catheter has a low cross-sectional area so that the catheter may be deployed in arteries and other body lumen with small diameters. Prior to delivery of the medication or other substance between two lobes of the multi-lobed balloon catheter, the fluid in the body lumen could be removed via suction on the delivery lumen 72.

Figure 11:
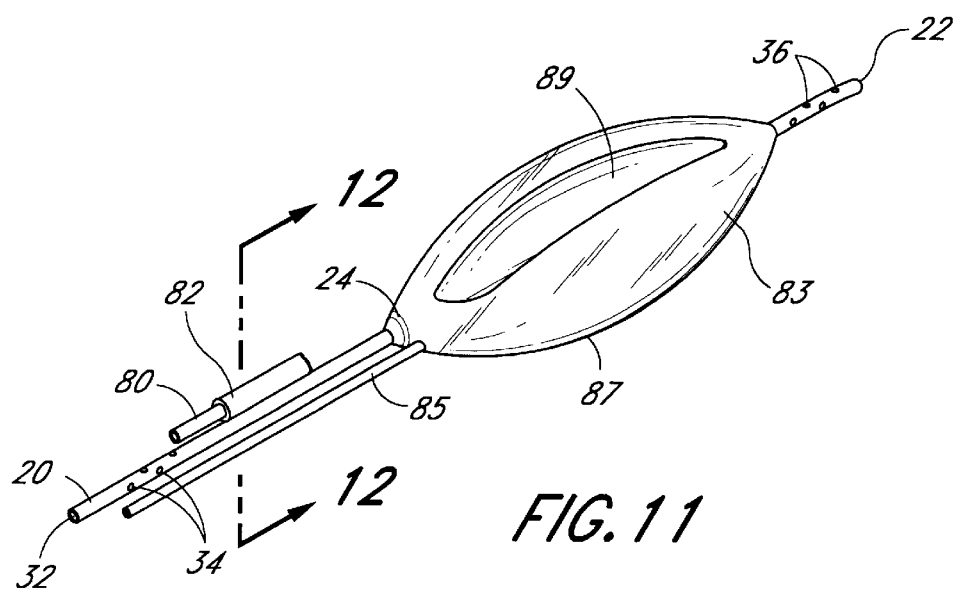
FIG. 11 illustrates yet another embodiment of a balloon catheter in accordance with the present invention.
Figure 12:
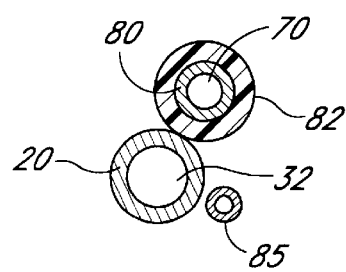
FIG. 12 is a cross-sectional view of the balloon catheter illustrated in FIG. 10 along 12—12 in FIG. 11.

FIGS. 11 and 12 illustrate another embodiment of the invention. In this embodiment, a second wire 80 is movably secured to the wire 20. The second wire 80 may be held to the wire 20 using a thin membrane 82. The membrane 82 may cover the second wire 80 along its entire length or may instead cover portions of the second wire 80 at intervals along the length thereof. The second wire 80 is located adjacent one side of the hollow wire 20, as shown in FIG. 11. Preferably, the second wire follows a proximal end 83 of the balloon 12, which is mounted directly to the wire 20, so as not to enlarge the cross-sectional area of a balloon 87. In one embodiment the balloon 87 has a depression or slot 89 which allows the wire 80 to advance. Influent and effluent ports 34 and 36 are provided in the first wire 22 in the manner described above with reference to the previous embodiments. An inflation lumen 85 in fluid communication with the balloon 87 and extending the length of the catheter, provides inflation media for the balloon 87.

The embodiment illustrated in FIGS. 11 and 12 is particularly suited for distal arteries or for blood vessel areas that have severe stenosis. The catheter is inserted into the blood vessel until the balloon lies adjacent the stenotic area of the vessel. As discussed, the second wire 80 follows the proximal end of the balloon so as not to enlarge the profile of the catheter 10. The balloon 82 is then inflated a desired number of times and withdrawn from the stenotic region, while the second wire 80 is simultaneously advanced beyond the stenotic region. The wire 80 is left in place in the blood vessel for a desired period of time to ensure that the blood vessel does not collapse. If the vessel collapses, the wire 80 is still in place and provides ready access to the stenotic region so that another catheter may be passed across the stenotic region using the second wire 80.

Figure 13:
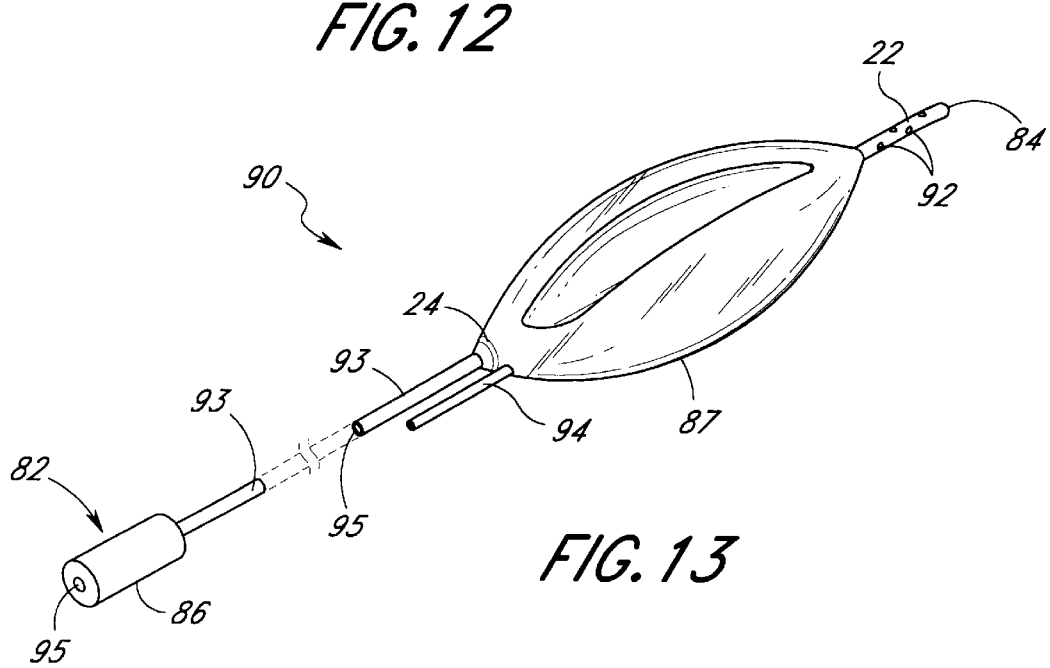
FIG. 13 illustrates another embodiment of the present invention.

FIG. 13 depicts yet another embodiment of the present invention. A catheter 90 has a proximal end 82 and a distal end 84 with the balloon 82 mounted directly to a wire 93 to provide a low profile. A manifold 86 is located at the proximal end of the catheter 80 and is in fluid communication with a hollow passage 95 within the wire 93. One or more effluent ports 92 are located distal of the balloon 12. The effluent ports 92 are in fluid communication with the passage 32. Preferably, the catheter 90 may be used for active perfusion or syringe forced flow to a location of the artery distal of the balloon 87. Blood or medication may be forced into passage 95 through the manifold 86. The blood or medication preferably flows through the passage 95 and exits through the effluent ports 92 at the distal end 84 of the catheter 90. In this manner, the catheter may be positioned so that the distal end 84 is located within an artery and the proximal end 82 is located outside the patient's body. Blood or drugs may be introduced into the passage 95 through the manifold 86 and transferred to the distal end 84. The blood or drugs exit the passage through the effluent ports 92. In addition, an axial aperture could be provided at the distal end 84 of the wire 13.

An inflation lumen 94 is in fluid communication with the balloon and extends along the catheter to the proximal portion of the catheter to provide inflation media for the balloon 87.

Although the preferred embodiment of the present invention has disclosed the features of the invention as applied to these embodiments, it will be understood that various omissions, substitutions, and changes in the form of the detail of the embodiments illustrated may be made by those skilled in the art without departing from the spirit of the present invention. Consequently, the scope of the invention should not be limited to the foregoing disclosure, but is to be defined by the claims which follow.

What is claimed is:

1. A stent for placement within a body lumen comprising:
   a mesh material, said mesh material adapted to form a tube-like stent having a hexagonal cross-section.

2. The stent of claim 1, wherein said stent comprises an ostial stent.

3. The stent of claim 2, wherein said stent is coated with heparin.

4. The stent of claim 1, wherein said stent is expandable and adapted for positioning on an inflation balloon attached to a catheter.

5. The stent of claim 4, wherein said stent is an ostial stent coated with heparin.

* * * * *